US00PP33899P2

(12) United States Plant Patent
Ranney et al.

(10) Patent No.: US PP33,899 P2
(45) Date of Patent: Jan. 25, 2022

(54) ***VIBURNUM* PLANT NAMED 'NCVP1'**

(50) Latin Name: ***Viburnum* hybrid**
Varietal Denomination: NCVP1

(71) Applicant: North Carolina State University, Raleigh, NC (US)

(72) Inventors: Thomas Green Ranney, Arden, NC (US); Darren Touchell, Raleigh, NC (US); Irene Palmer, Raleigh, NC (US); Andra Nus, Raleigh, NC (US); Nathan P. Lynch, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 17/342,802

(22) Filed: Jun. 9, 2021

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/02; A01H 5/00
See application file for complete search history.

(56) References Cited

PUBLICATIONS https://www.gardendesignonline.com/gardendesignonline/2021/01/new-plants-2021-ii-.html; Jan. 14, 2021; 1 page.*

* cited by examiner

*Primary Examiner* — Kent L Bell
(74) *Attorney, Agent, or Firm* — Cassandra Bright

(57) ABSTRACT

A new and distinct cultivar of *Viburnum* plant named 'NCVP1' with a compact habit, and white flowers in spring that rebloom in summer. 'NCVP1' is a new cultivar of doublefile *Viburnum*, suitable for ornamental garden purposes.

3 Drawing Sheets

Latin name of the genus and species: *Viburnum* hybrid.
Variety denomination: 'NCVP1'.

BACKGROUND OF THE INVENTION

The present invention comprises a new and distinct doublefile *Viburnum* cultivar hereinafter referred to by the cultivar name 'NCVP1'. This new doublefile *Viburnum* was developed through a breeding program at Mills River, N.C. 'NCVP1' was selected from an $F_2$ population of seedlings derived from *Viburnum plicatum tomentosum* H2008-058-076 ('Molly Schroeder' x 'Summer Snowflake')(not patented). The first asexual propagation of 'NCVP1' was carried out in July 2013 by rooting stem cuttings at a research greenhouse in Mills River, N.C. and has been asexually reproduced repeatedly by vegetative cuttings over a 8-year period. 'NCVP1' roots readily from softwood cuttings treated with a basal dip of 3,000-4,000 ppm indole butyric acid (potassium salt) in water. 'NCVP1' has been found to retain its distinctive characteristics through successive asexual propagations.

SUMMARY OF THE INVENTION

The following are the unique combination of characteristics of this new cultivar when grown under standard horticultural practices at a research greenhouse in Mills River, N.C.

1. A compact habit with dense branching.
2. Abundant white flowers in spring with repeat blooming in summer.
3. Burgundy-red fall foliage color.

COMPARISON WITH PARENT VARIETIES

Records of the parent variety characteristics are not available. The inventor cannot make a comparison to the seed parent. The pollen parent is unknown.

COMPARISON WITH COMMERCIAL CULTIVARS

'NCVP1' is distinguished from *Viburnum plicatum* f. *tomentosum* 'Summer Snowflake'(unpatented) in that 'NCVP1' has a smaller, more compact habit to 120 cm tall and wide, whereas *V. plicatum* f. *tomentosum* 'Summer Snowflake' grows to about 200 cm tall. 'NCVP1' is distinguished from *V. plicatum* f. *tomentosum* 'Mariesii'(unpatented) in that 'Mariesii' will grow taller and wider than 200 cm tall, and 'NCVP1' will remain compact. 'NCVP1' is distinguished from *Viburnum plicatum* f. *tomentosum* 'Molly Schroeder' (unpatented) in that 'NCVP1' has pure white sterile flowers and *V. plicatum* f. *tomentosum* 'Molly Schroeder' has pink sterile flowers. 'NCVP1' is distinguished from 'SMNVPTFD', U.S. Plant Pat. No. 29,553 in having a larger habit (120 cm tall and wide) compared to 60 to 90 cm and 90 to 120 cm wide habit of SMNVPTFD'. The plant habit of 'NCVP1' is globose and upright, whereas the habit of 'SMNVPTFD' is more horizontally spreading. The new variety does not form fruit; 'SMNVPTFD' forms berries in the Fall.

BRIEF DESCRIPTION OF THE PHOTOGRAPHS

This new doublefile *Viburnum* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *Viburnum*. Plants in the photographs are approximately 2 years old.

DETAILED BOTANICAL DESCRIPTION

Figure 1:
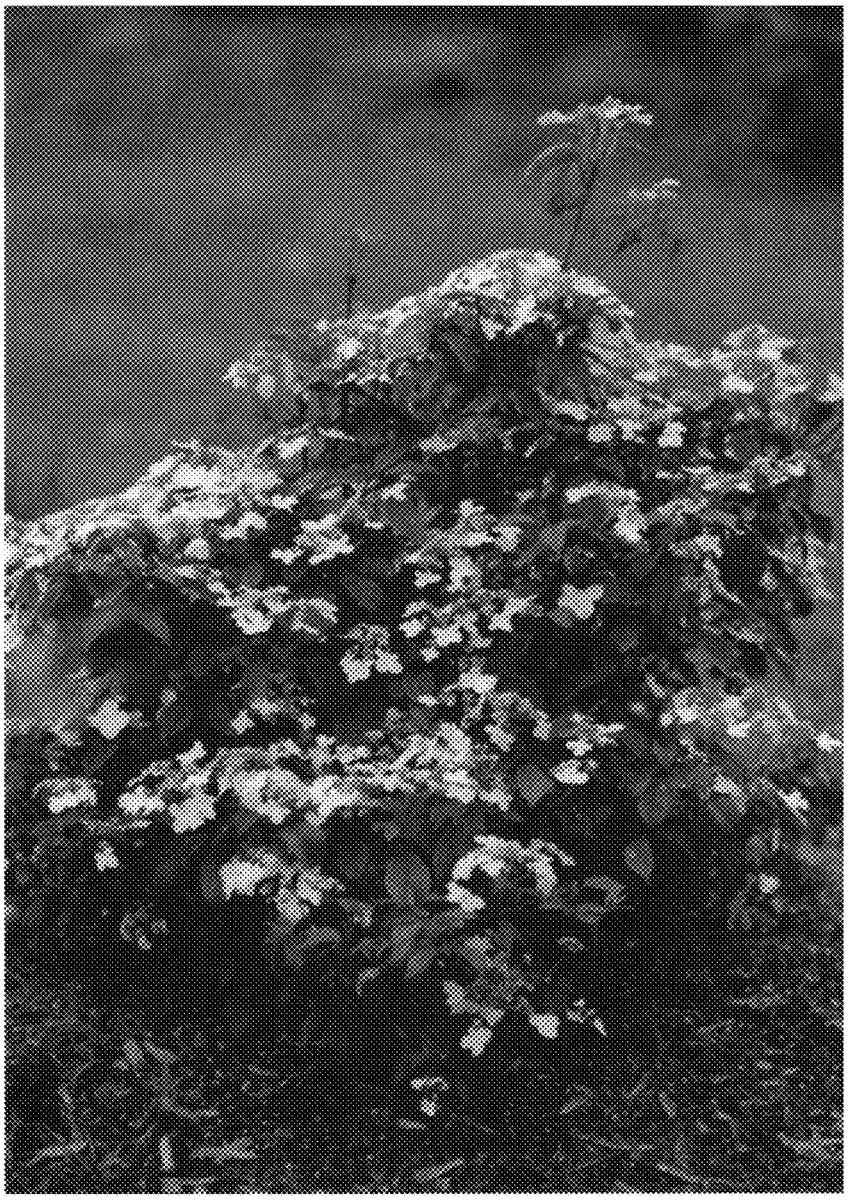
FIG. 1 is a photograph showing a field-grown plant with white inflorescences in Spring 2020 in Grand Haven, Mich.
Figure 2:
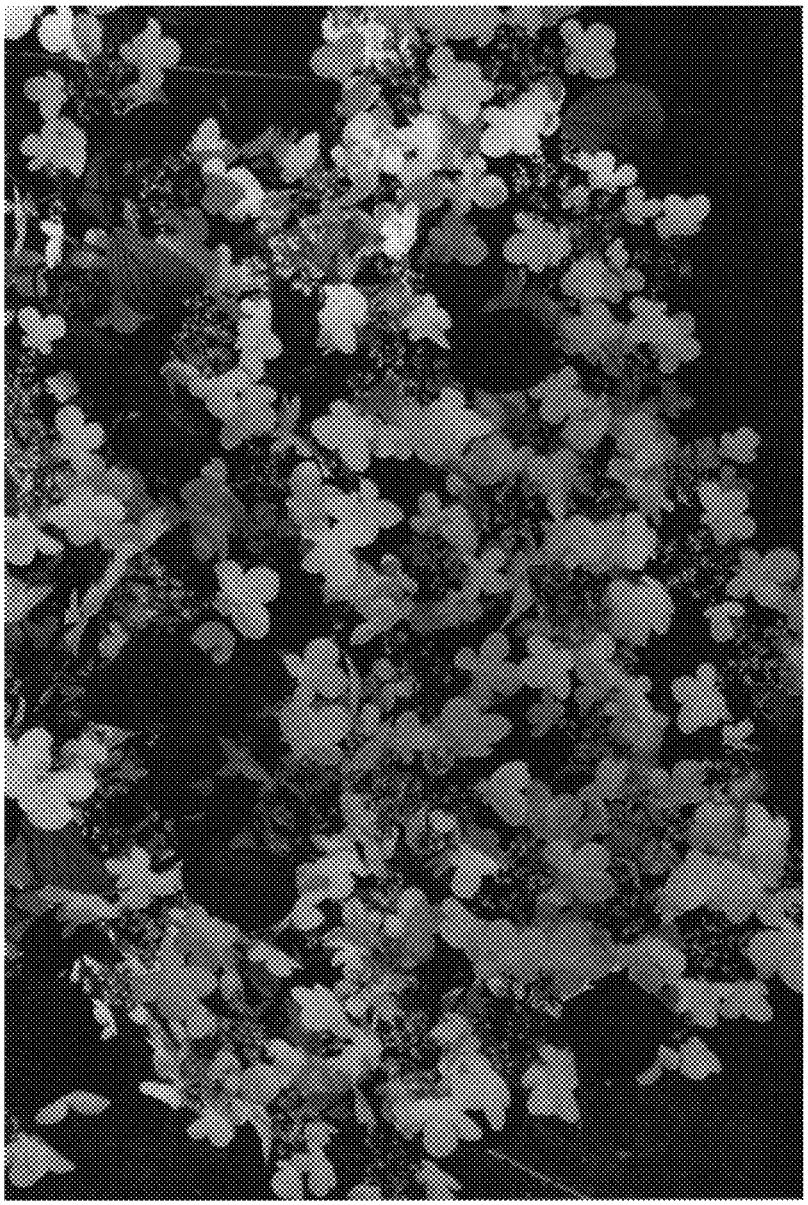
FIG. 2 is a photograph showing the high floral coverage and compact habit of 'NCVP1' taken in Spring 2020 in Grand Haven, Mich.
Figure 3:
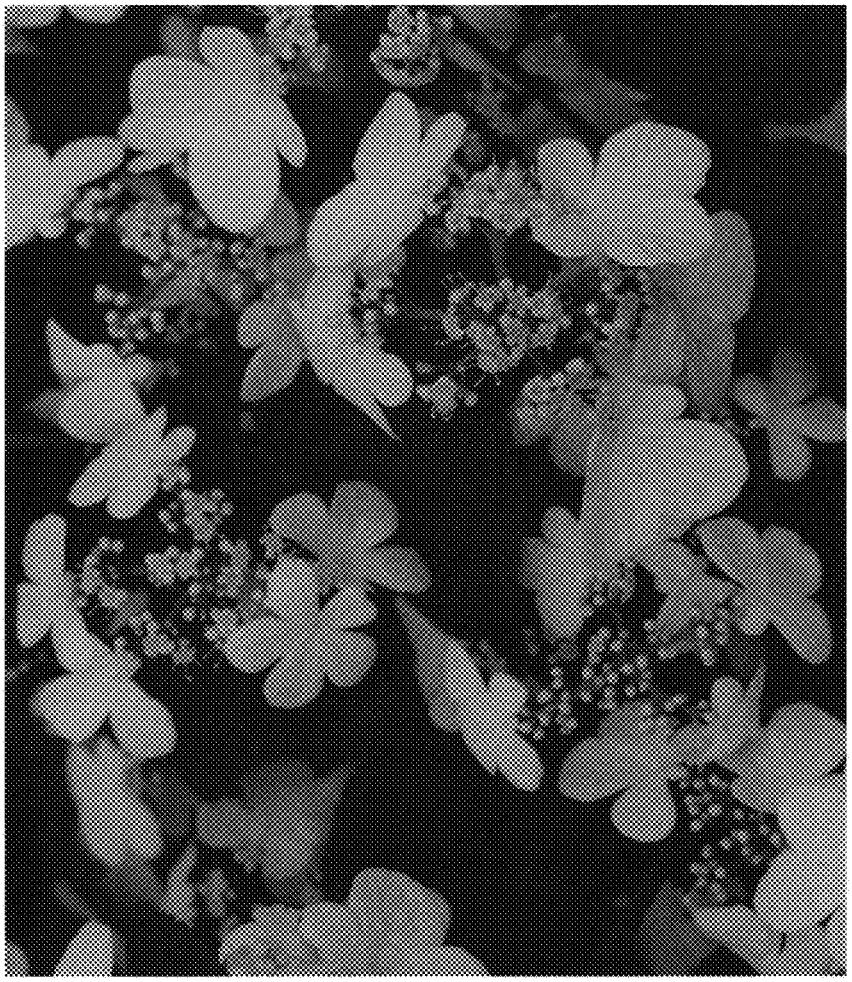
FIG. 3 is a photograph of the sterile and fertile flowers of 'NCVP1' taken in Mills River, N.C. on Mar. 2, 2021 in a greenhouse.

The following is a detailed description of the botanical characteristics of the new and distinct doublefile *Viburnum* cultivar known by the denomination 'NCVP1'. The detailed description was taken on a two-year-old container-grown plant in Mills River, N.C. and six-year-old plants in Grand Haven, Mich. in 2020. All colors cited herein refer to The Royal Horticultural Society Colour Chart (The Royal Horticultural Society (R.H.S.), London, Sixth Edition). Where specific dimensions, sizes, colors, and other characteristics are given, it is to be understood that such characteristics are approximations or averages set forth as accurately as practicable.

PLANT

Growth habit: Densely branched, compact, globose with tiered branches.

Height:
- *Two-year-old container-grown plant.*—25 cm.
- *Six-year-old field-grown plants.*—120 cm.

Width:
- *Two-year-old container-grown plant.*—30 cm.
- *Six-year-old field-grown plants.*—120 cm.

Stems, shoots, branches, trunk:
- *Shoots* (*current year's growth*).—Shape: Rounded. Shoot length: Average 6.8 cm (4 to 10.5 cm). Shoot diameter: About 0.2 cm. Color: Grey-Brown (199B). Texture: Pubescent.
- *Shoots* (*prior year's growth*).—Shape: Rounded. Stem length: Avg. 15 cm (9 to 28 cm). Stem diameter: Avg. 2.7 cm (2 to 3 cm). Color: Grey-Brown (199A). Texture: Glabrous with lenticels.
- *Branches* (*woody branches* 2-4 *years old*).—Shape: Rounded. Branch length: Avg. 26.8 cm (21 to 40 cm). Branch diameter: Avg 1.0 cm (0.8 to 1.3 cm). Color: Grey-Brown (199A). Texture: Glabrous with vertical fissures.
- *Internode length.*—Avg. 4 cm (2 to 7 cm).

FOLIAGE

Type: Simple.
Persistence: Deciduous.
Arrangement: Opposite.
Shape: Ovate.
Length of lamina: Avg. 8.5 cm (5 to 12 cm).
Width: Avg. 4.5 cm (3.5 to 5.5 cm).

Emerging leaves:
- *Color.*—Upper: Green (137A) flushed with Red-Purple (59B). Lower: Yellow-Green (146B) flushed with Greyed-Purple (186D).
- *Texture.*—Pubescent.

Mature leaves during growing season:
- *Color.*—Upper: Green (137A). Lower: Yellow-Green (146B).
- *Texture.*—Upper: Glabrous. Lower: Pubescent.

Fall foliage:
- *Color.*—Red-Purple (61A), upper and lower surfaces.

Apex: Acute.
Base: Cuneate.
Margins: Serrate.
Venation: Pinnate.
- *Vein color.*—Upper: Green (137A). Lower: Red-Purple (58A).

Leaf attachment: Petiolate.
- *Petiole.*—Length: Avg. 0.8 cm (0.6 to 1 cm). Diameter: About 0.1 cm. Color: Red-Purple (58A). Texture: Pubescent.

INFLORESCENCE

Description: Flowers arranged in terminal flat-topped cymes, with inner fertile flowers and outer sterile flowers.
Flowering season: May in Mills River, N.C.
Number of inflorescences per plant: About 50 per three-gallon containerized plant.
Number of flowers per inflorescence: About 100.
Fragrance: None.

Inflorescence:
- *Diameter.*—Avg. 15 cm (10 to 18 cm).
- *Height.*—Avg. 7.5 cm (5 to 8 cm).

Flower bud:
- *Shape.*—Rounded.
- *Length.*—About 0.1 cm.
- *Diameter.*—About 0.1 cm.
- *Color.*—Yellow-Green (145C).

Flower:
- *Fertile flower diameter.*—About 0.4 cm.
- *Fertile flower height.*—About 0.2 cm.
- *Sterile flower diameter.*—Avg. 2.6 cm (1.8 to 3.5 cm).
- *Sterile flower height.*—About 0.2 cm.

Petals:
- *Arrangement.*—Whorled.
- *Fertile flowers.*—Number of petals per fertile flower: 5. Shape: Ovate. Length: About 0.1 cm. Width: About 0.1 cm. Color: Green-White (157C). Texture: Glabrous all surfaces. Apex: Obtuse. Base: Fused. Margin: Entire.
- *Sterile flowers.*—Number of petals per sterile flower: 4 to 5. Shape: Rounded. Length: Avg. 1.2 cm (1.1 to 1.4 cm). Width: Avg. 1.0 cm (0.8 to 1.4 cm). Color: Green-White (157D). Texture: Glabrous all surfaces. Apex: Rounded. Base: Fused. Margin: Entire.

Sepal:
- *Number.*—5 fused sepals.
- *Arrangement.*—Whorled.
- *Shape.*—Ovate.
- *Length.*—Less than 0.1 cm.
- *Width.*—Less than 0.1 cm.
- *Color.*—Yellow-Green (144D) upper and lower surfaces.
- *Texture.*—Slightly pubescent all surfaces.
- *Apex.*—Acute.

*Base*.—Fused.
*Margin*.—Entire.

Peduncle:
*Length*.—About 7.5 cm.
*Diameter*.—About 0.15 cm.
*Color*.—Close to Yellow-Green (152C).
*Texture*.—Pubescent.

Pedicels:
*Length*.—About 0.5 cm.
*Diameter*.—Less than 0.1 cm.
*Color*.—Close to Yellow-Green (145A).
*Texture*.—Pubescent.

REPRODUCTIVE ORGANS

Gynoecium:
*Pistil number*.—1.
*Pistil length*.—About 0.1 cm.
*Stigma shape*.—Rounded.
*Stigma color*.—Green-White (157B).
*Style length*.—Less than 0.1 cm.
*Style color*.—Green-White (157B).

Androecium:
*Stamen number*.—5.
*Anther shape*.—Rounded.
*Anther size*.—Less than 0.1 cm.
*Anther color*.—Green-White (157B).
*Amount of pollen*.—Average.
*Pollen color*.—Yellow (5A).

OTHER CHARACTERISTICS

Fruit and seed: None observed.

Disease and insect resistance: No significant disease or insect pests have been observed.

Cold hardiness: At least USDA zone 6b; testing has not been completed in colder zones.

What is claimed is:

1. A new and distinct cultivar of *Viburnum* plant named 'NCVP1' as illustrated and described herein.

* * * * *